US012307665B2

(12) United States Patent
Choi et al.

(10) Patent No.: US 12,307,665 B2
(45) Date of Patent: May 20, 2025

(54) METHOD AND DEVICE FOR QUANTIFYING SIZE OF TISSUE OF INTEREST OF ANIMAL BY USING X-RAY IMAGE OF ANIMAL

(71) Applicants: Woorien Co., Ltd., Gyeonggi-do (KR); VATECH EWOO Holdings Co., Ltd., Gyeonggi-do (KR)

(72) Inventors: In Choi, Gyeonggi-do (KR); Tae Hee Han, Gyeonggi-do (KR)

(73) Assignees: Woorien Co., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 389 days.

(21) Appl. No.: 17/828,275

(22) Filed: May 31, 2022

(65) Prior Publication Data
US 2022/0383493 A1 Dec. 1, 2022

(30) Foreign Application Priority Data

May 31, 2021 (KR) .......................... 10-2021-0070435

(51) Int. Cl.
*G06T 7/00* (2017.01)
*A61B 6/46* (2024.01)
(Continued)

(52) U.S. Cl.
CPC ............ *G06T 7/0012* (2013.01); *A61B 6/463* (2013.01); *A61B 6/469* (2013.01); *A61B 6/503* (2013.01);
(Continued)

(58) Field of Classification Search
CPC ..... G06T 7/0012; G06T 7/60; G06T 2200/24; G06T 2207/10116; G06T 2207/30012;
(Continued)

(56) References Cited

U.S. PATENT DOCUMENTS

| 2016/0314601 | A1* | 10/2016 | Sankaran .............. G06T 7/0012 |
| 2018/0114314 | A1* | 4/2018 | Butler ....................... G06T 5/70 |
| 2020/0229783 | A1 | 7/2020 | Jung |

FOREIGN PATENT DOCUMENTS

| KR | 10-2006-0008849 A | 1/2006 |
| KR | 10-2020-0090102 A | 7/2020 |
| WO | 2014/198753 A1 | 12/2014 |

OTHER PUBLICATIONS

Rebecca Stepien et al. "Use of radiographic measurements to diagnose stage B2 preclinical myxomatous mitral value disease in dogs", AVMA Publications, vol. 256: Issue 10, DOI: https://doi.org/10.2460/javma.256.10.1129, Online Publication date: May 15, 2020. (Year: 2020).*

* cited by examiner

*Primary Examiner* — John J Lee
(74) *Attorney, Agent, or Firm* — IP Legal Services, LLC

(57) ABSTRACT

A method of quantifying a size of a tissue of interest in a animal through a device including a storage, an image processor, and a display by using an X-ray image of the animal is proposed. The proposed method may include storing the X-ray image in the storage, displaying the X-ray image on the display, performing, by the image processor, processes of (i) calculating a reference value for a length of a reference tissue of the animal displayed on the X-ray image, (ii) calculating a value of a length in at least one specific direction of the tissue of interest of the animal displayed on the X-ray image, and (iii) quantifying the size of the tissue of interest as a ratio of the value of the length to the reference value, and displaying the quantified size of the tissue of interest on the display.

8 Claims, 13 Drawing Sheets

(51) Int. Cl.
 *A61B 6/50* (2024.01)
 *G06T 7/60* (2017.01)
(52) U.S. Cl.
 CPC ............... *A61B 6/505* (2013.01); *G06T 7/60* (2013.01); *G06T 2200/24* (2013.01); *G06T 2207/10116* (2013.01); *G06T 2207/30012* (2013.01); *G06T 2207/30048* (2013.01)
(58) Field of Classification Search
 CPC .......... G06T 2207/30048; A61B 6/463; A61B 6/469; A61B 6/503; A61B 6/505
 See application file for complete search history.

METHOD AND DEVICE FOR QUANTIFYING SIZE OF TISSUE OF INTEREST OF ANIMAL BY USING X-RAY IMAGE OF ANIMAL

CROSS REFERENCE TO RELATED APPLICATION

The present application claims priority to Korean Patent Application No. 10-2021-0070435, filed May 31, 2021, the entire contents of which is incorporated herein for all purposes by this reference.

BACKGROUND OF THE INVENTION

Field of the Invention

The present disclosure relates to a technology for processing an X-ray image and, more particularly, to a technology for quantifying a size of a tissue of interest in a animal by using an X-ray image of the animal.

Description of the Related Art

A radiographic technique for non-destructively examining symptoms of a disease of a animal is known. For example, a size of the heart shown on an X-ray image of the animal is used to examine a heart failure of the animal, and in this case, when the size of the heart of a target animal is abnormally large compared to the size of the normal heart of another animal of the same type, the target animal may be diagnosed with cardiomegaly. However, since animals have various body types and heart shapes, it is difficult to diagnose cardiomegaly on the basis of only an absolute size of the heart. For this reason, diagnostic methods for diagnosing cardiomegaly by converting a length of the heart shown on the X-ray image of the animal to a length of another tissue are being used. As the most representative method among the diagnostic methods, a Vertebral Heart Scale (VHS) index and a Vertebral Left Atrial Score (VLAS) index are known. Each of these indexes represents a numerical value corresponding to the number of thoracic vertebrae shown in an X-ray image corresponding to a length of the heart shown on the same X-ray image of a animal, that is, a numerical value obtained by converting the length of the heart shown on the X-ray image of the animal into the number of thoracic vertebrae. However, such diagnostic methods are not without problems. In order to convert the length of the heart shown on the X-ray image of the animal into the number of thoracic vertebrae, the thoracic vertebrae shown on the X-ray image should be arranged in a straight line. During X-ray imaging of the animal, there are many cases where the thoracic vertebrae are bent on the X-ray image of the animal depending on imaging postures of the animal. For this reason, the number of thoracic vertebrae, shown on the same X-ray image, corresponding to the length of the heart shown on the X-ray image of the animal does not match the actual number of thoracic vertebrae, resulting in errors in the obtained numerical values of the VHS index and numerical value of the VLAS index.

SUMMARY OF THE INVENTION

An objective of the present disclosure for solving the problems is to provide a technique in which a size of a tissue of interest of a animal is quantified by using an X-ray image of the animal, so that an error in terms of the size of the tissue of interest quantified by using the X-ray image of the animal is not large regardless of imaging postures of the animal.

The problems to be solved by the present disclosure are not limited to the problems mentioned above, and other problems not mentioned herein will be clearly understood by those skilled in the art from the following description.

In one aspect, there is provided a method of quantifying a size of a tissue of interest of a animal through a device configured to include a storage, an image processor, and a display by using an X-ray image of the animal, the method including: storing the X-ray image in the storage; displaying the X-ray image on the display; performing, by the image processor, processes of (i) calculating a reference value for a length of a reference tissue of the animal displayed on the X-ray image, (ii) calculating a value of a length in at least one specific direction of the tissue of interest of the animal displayed on the X-ray image, and (iii) quantifying the size of the tissue of interest as a ratio of the value of the length to the reference value; and displaying the quantified size of the tissue of interest on the display.

In another aspect, there is provided a device for quantifying a size of a tissue of interest of a animal by using an X-ray image of the animal, the device including: a storage configured to store the X-ray image; a display; and an image processor configured to calculate a reference value for a length of a reference tissue shown on the X-ray image, calculate a value of a length in at least one specific direction of the tissue of interest of the animal by using the X-ray image, and quantify the size of the tissue of interest by a ratio of a value of the length to the reference value, wherein the image processor may be further configured to control the X-ray image and the quantified size of the tissue of interest to be displayed on the display.

According to the exemplary embodiments of the present disclosure, there is provided a technical effect in which the size of the tissue of interest the animal is quantified by using the X-ray image of the animal, so that the error in terms of the size of the tissue of interest quantified by using the X-ray image of the animal is not large regardless of the imaging postures of the animal.

DETAILED DESCRIPTION OF THE INVENTION

Hereinafter, an exemplary embodiment of the present disclosure will be described in detail with reference to the accompanying drawings. However, in the following description, when there is concern of unnecessarily obscuring the gist of the present disclosure, detailed descriptions of well-known functions or configurations will be omitted.

Figure 1:
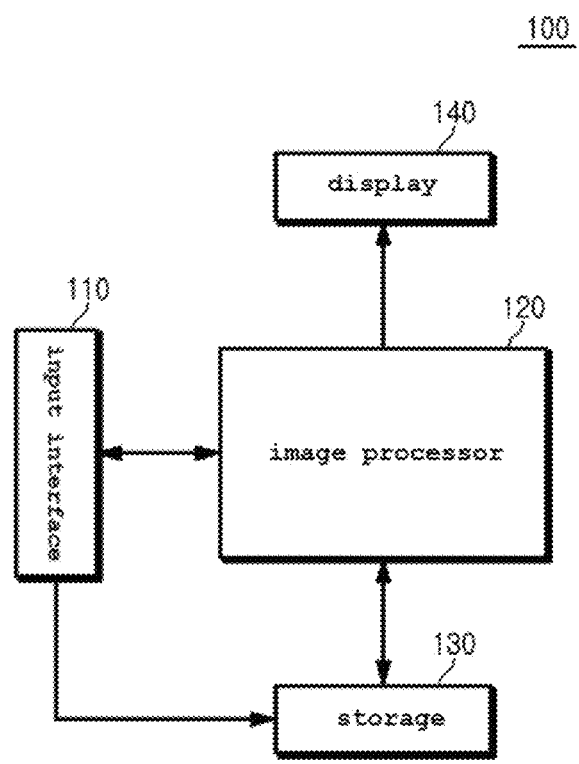
FIG. 1 is a view illustrating an exemplary embodiment of a block diagram of a device for quantifying a size of a tissue of interest in a animal by using an X-ray image of the animal.

FIG. 1 is a view illustrating an exemplary embodiment of a block diagram of a device for quantifying a size of a tissue of interest in a animal by using an X-ray image of the animal.

As shown in FIG. 1, a device 100 may include an input interface 110, an image processor 120, a storage 130, and a display 140. The input interface 110 may be configured to include hardware modules and software modules for inputting user instructions in order to perform image processing according to various exemplary embodiments of the present disclosure. The input interface 110 may be advantageously used to input various necessary instructions to the image processor 120, or input various image data such as animal's X-ray image data obtained by X-ray imaging to the storage 130, or perform various image processing accordingly by indicating some or all of a displayed X-ray image. The input interface 110 may be advantageously used to receive user inputs specifying various lengths on the X-ray image of the animal. The input interface 110 may also be advantageously used to specify and input, on the X-ray image of the animal, arbitrary points such as a ventral boundary point of a carina of the animal, and a ventral contact point of the heart-vena cava. The display 140 is for displaying various images according to various exemplary embodiments of the present disclosure, and may include various display devices such as an LCD display, an LED display, an AMOLED display, and a CRT display.

The storage 130 may be used to store data of various images, such as X-ray images obtained by the X-ray imaging of the animal. The storage 130 may be used to store: image data of intermediate results obtained by performing image processing according to various exemplary embodiments of the present disclosure; image data of results obtained by performing the image processing according to the various exemplary embodiments of the present disclosure; and variable values necessary to perform the image processing according to the various exemplary embodiments of the present disclosure. In various exemplary embodiments, the storage 130 may store the above-described various images in a Digital Imaging and Communications in Medicine (DI-COM) format, or a general image file format (i.e., BMP, JPEG, TIFF, etc.).

The image processor 120 may be configured to quantify a size of a tissue of interest of a animal by applying a method in which an error in terms of the size of the tissue of interest quantified by using an X-ray image of the animal is not large regardless of imaging postures of the animal. To this end, the image processor 120 is configured to quantify the size of the tissue of interest of the animal in a method of converting a length of the tissue of interest of the animal shown on the X-ray image of the animal into the number of reference tissues of the animal shown on the X-ray image of the animal. Here, the tissue of interest of the animal is a tissue of a target whose size is to be quantified, and the reference tissue of the animal is a tissue used as a reference in order to quantify the size of the tissue of interest of the animal. In the exemplary embodiment, the reference tissue of the animal is a specific thoracic vertebra of the animal and the tissue of interest of the animal is the heart of the animal. In the exemplary embodiment, considering that respective sizes (i.e., lengths) of fourth to seventh thoracic vertebrae of the animal are substantially uniform, any one of the thoracic vertebrae is selected as the reference tissue of the animal.

The image processor 120 may be configured to calculate a reference value for the reference tissue of the animal by using the X-ray image of the animal in order to quantify the size of the tissue of interest in the animal. In the exemplary embodiment, the image processor 120 is configured to automatically detect a region representing a specific thoracic vertebra of the animal on the X-ray image of the animal by using an image processing technique such as an edge detection algorithm, and automatically calculate a value of a length of the region representing the specific thoracic vertebra of the animal. In the exemplary embodiment, the image processor 120 is configured to detect the region representing the specific thoracic vertebra of the animal by using the image processing technique such as the edge detection algorithm, and calculate the value of the length of the region representing the specific thoracic vertebra of the animal in response to receiving a user input pointing to the specific thoracic vertebra of the animal on the X-ray image of animal through the input interface 110. In the exemplary embodiment, the image processor 120 is configured to calculate the value of the length of the region representing the specific thoracic vertebra of the animal in response to receiving, through the input interface 110, a user input specifying the length of the region representing the specific thoracic vertebra of the animal on the X-ray image of the animal, that is, in response to detecting, through the input interface 110, a user motion of drawing a reference line corresponding to the length of the region representing the specific thoracic vertebra of the animal. In such an exemplary embodiment, a user may perform the motion of drawing a line as the reference line from a start point of the specific thoracic vertebra, which is a target for calculating the value of the length, to a disk between the corresponding thoracic vertebra and the next thoracic vertebra, that is, from the start point of the corresponding thoracic vertebra to a start point of the next thoracic vertebra. In addition, in such an exemplary embodiment, the value of the length of the region representing the specific thoracic vertebra of the animal is calculated as a value of a length of the reference line drawn by the user. In the exemplary embodiment, the image processor 120 is configured to control the calculated value of the length of the region representing the specific thoracic vertebra of the animal to be displayed, on the X-ray image of the animal, in the region representing the specific thoracic vertebra of the animal or at a position adjacent to the reference line.

The image processor 120 may be further configured to calculate values of lengths in specific directions for the tissue of interest of the animal by using the X-ray image of the animal in order to quantify the size of the tissue of interest in the animal. In the exemplary embodiment, the image processor 120 is configured to automatically detect the region representing the heart of the animal by using the image processing technique such as the edge detection algorithm on the X-ray image of the animal, automatically calculate a value of a length in a long axis direction of the region representing the heart of the animal, and also automatically calculate a value of a length in a short axis direction perpendicular to the long axis direction of the region representing the heart of the animal. In the exemplary embodiment, the image processor 120 is configured to automatically detect a region representing the left atrium of the heart of the animal by using the image processing technique such as the edge detection algorithm on the X-ray image of the animal, and automatically calculate a value of a length of the region representing the left atrium of the heart of the animal.

In the exemplary embodiment, the image processor 120 is further configured to calculate the value of the length in the long axis direction of the region representing the heart of the animal in response to receiving a user input specifying the length in the long axis direction of the region representing the heart of the animal on the X-ray image of the animal through the input interface 110, that is, in response to detecting a user motion of drawing a reference line corresponding to the length in the long axis direction in the region representing the heart of the animal through the input interface 110. In such an exemplary embodiment, the user may perform the motion of drawing a line as the reference line from a point (i.e., a reference point) of the ventral boundary of the carina to the apex of the heart (i.e., an end of the heart furthest from the reference point). In addition, in such an exemplary embodiment, the value of the length in the long axis direction of the region representing the heart of the animal is calculated as a value of a length of the reference line drawn by the user. In the exemplary embodiment, the image processor 120 is configured to control the calculated value of the length in the long axis direction of the region representing the heart of the animal to be displayed at a position adjacent to the reference line on the X-ray image of the animal.

In the exemplary embodiment, the image processor 120 is further configured to calculate the value of the length in the short axis direction of the region representing the heart of the animal in response to receiving a user input specifying the length in the short axis direction of the region representing the heart of the animal on the X-ray image of the animal through the input interface 110, that is, in response to detecting a user motion of drawing a reference line corresponding to the length in the short axis direction in the region representing the heart of the animal through the input interface 110. In such an exemplary embodiment, the user may perform the motion of drawing a line as the reference line from a ventral contact point (i.e., a reference point) of the heart-aorta to a boundary point of the heart, so as to be perpendicular to a predetermined length line in the long axis direction. In addition, in such an exemplary embodiment, the value of the length in the short axis direction of the region representing the heart of the animal is calculated as a value of a length of the reference line drawn by the user. In the exemplary embodiment, the image processor 120 is configured to control the calculated value of the length in the short axis direction of the region representing the heart of the animal to be displayed at the position adjacent to the reference line on the X-ray image of the animal.

In the exemplary embodiment, the image processor 120 is configured to automatically detect the apex of the heart, so as to automatically calculate the value of the length in the long axis direction of the region representing the heart of the animal, in response to the user specifying a point on the ventral boundary of the carina of the animal as a reference point. In the exemplary embodiment, the image processor 120 is configured to automatically calculate a value of a length in a short axis direction perpendicular to a long axis direction in response to the user specifying a ventral contact point of the heart-aorta of the animal as a reference point.

In the exemplary embodiment, the image processor 120 is further configured to calculate the value of the length of the region representing the left atrium of the heart of the animal in response to receiving, through the input interface 110, a user input specifying the length of the region representing the left atrium of the heart of the animal on the X-ray image of the animal, that is, in response to detecting, through the input interface 110, a user motion of drawing a reference line corresponding to the length of the region representing the left atrium of the heart of the animal. In such an exemplary embodiment, the value of the length of the region representing the left atrium of the heart of the animal is calculated as a value of a length of the reference line drawn by the user. In the exemplary embodiment, the image processor 120 is configured to control the calculated value of the length of the region representing the left atrium of the heart of the animal to be displayed at a position adjacent to the reference line on the X-ray image of the animal.

In addition, in order to quantify the size of the tissue of interest in the animal, the image processor 120 is further configured to quantify the size of the tissue of interest in the animal as a ratio of the value of the length for the tissue of interest of the animal to the reference value of the reference tissue of the animal. In the exemplary embodiment, the image processor 120 is configured to calculate, as a Vertebral Heart Scale (VHS) index, a value of dividing a value obtained by adding the value of the length in the long axis direction of the region representing the heart of the animal to the value of the length in the short axis direction of the region representing the heart of the animal by the value of the length of the region representing the specific thoracic vertebra of the animal. In the exemplary embodiment, the image processor 120 is configured to calculate, as a Vertebral Left Atrial Score (VLAS) index, a value obtained by dividing a value of the length of the region representing the left atrium of the heart of the animal by the value of the length of the region representing the specific thoracic vertebra of the animal. In the exemplary embodiment, the image processor 120 is configured to compare the calculated VHS index and/or VLAS index with predetermined respective thresholds, and display a comparison result or a possibility of cardiomegaly of the animal based on the comparison result to the user through the display 140.

Figure 2:
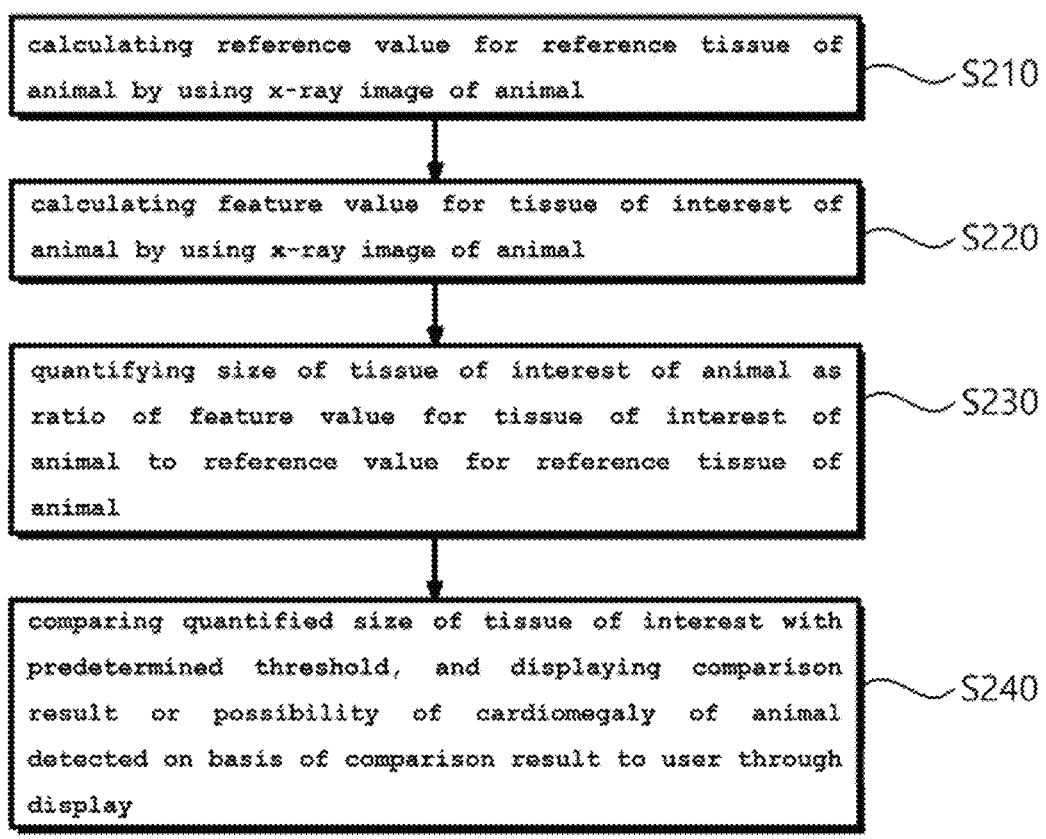
FIG. 2 is a view illustrating the exemplary embodiment of a flowchart for describing a method of quantifying a size of a tissue of interest in a animal by using an X-ray image of the animal.

FIG. 2 is a view illustrating the exemplary embodiment of a flowchart for describing a method of quantifying a size of a tissue of interest in a animal by using an X-ray image of the animal.

As shown in FIG. 2, the present method starts from step S210 of calculating a reference value for a reference tissue of a animal by using an X-ray image of the animal. As described above, a tissue of interest of the animal is a tissue of a target whose size is to be quantified, and the reference tissue of the animal is a tissue used as a reference in order to quantify a size of the tissue of interest in the animal. In the exemplary embodiment, the reference tissue of the animal is a specific thoracic vertebra of the animal and the tissue of interest of the animal is the heart of the animal. In the exemplary embodiment, considering that respective sizes (i.e., lengths) of fourth to seventh thoracic vertebrae of the animal are substantially uniform, any one of the thoracic vertebrae is selected as the reference tissue of the animal. However, the reference tissue is not necessarily limited to one of the first to seventh thoracic vertebrae, and any one thoracic vertebra clearly identifiable on an X-ray image may be selected when necessary.

Figure 3:
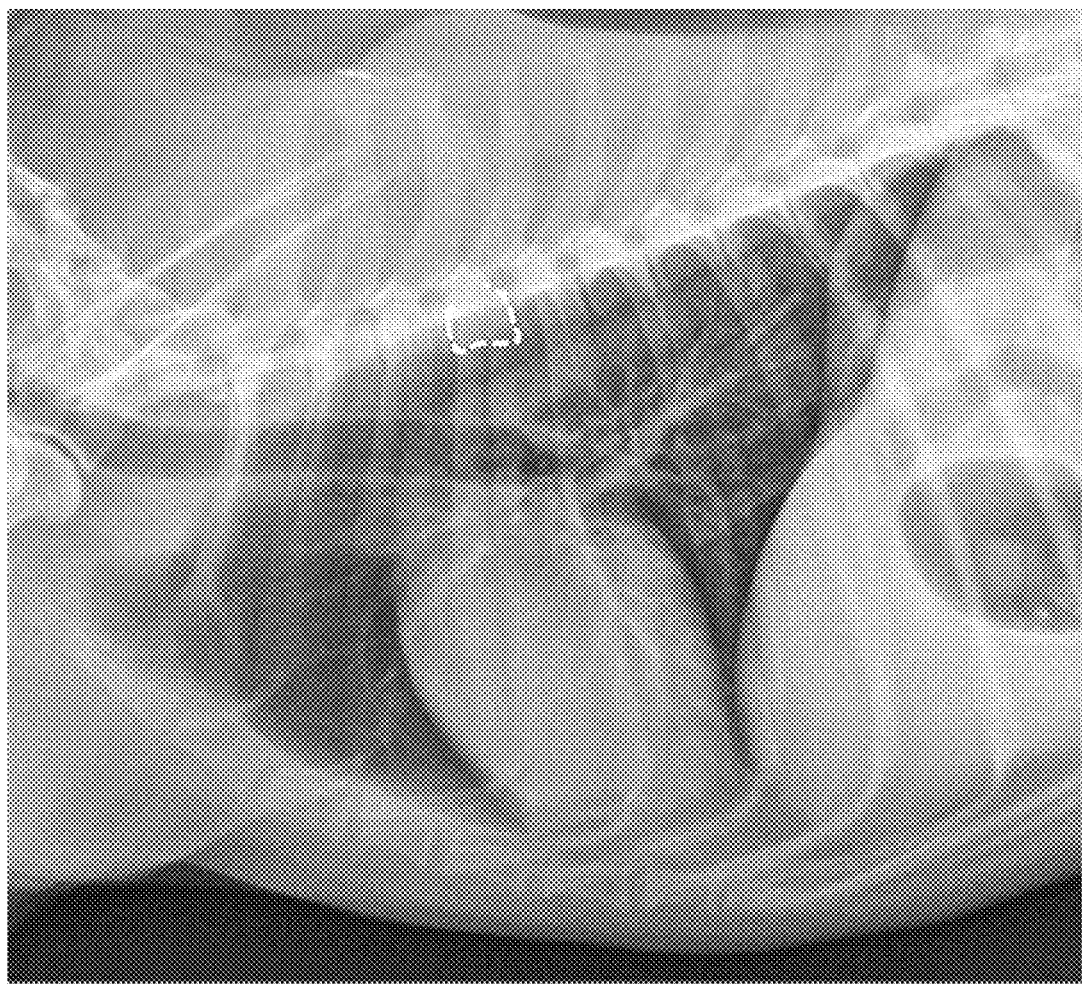
FIG. 3 is a view illustrating a region representing a specific thoracic vertebra of the animal automatically detected on the X-ray image of the animal.
Figure 4:
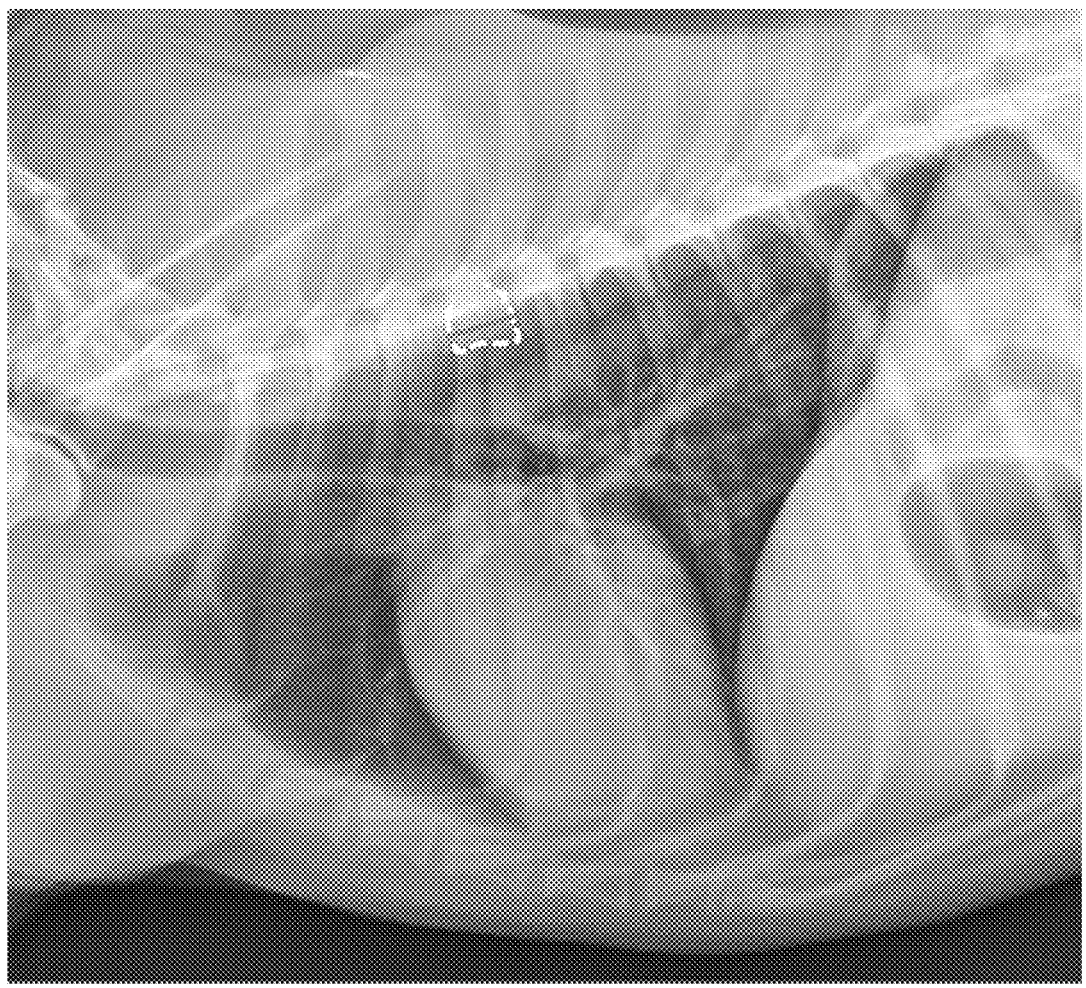
FIG. 4 is a view illustrating a reference line drawn by a user in the region representing the specific thoracic vertebra of the animal.
Figure 5:
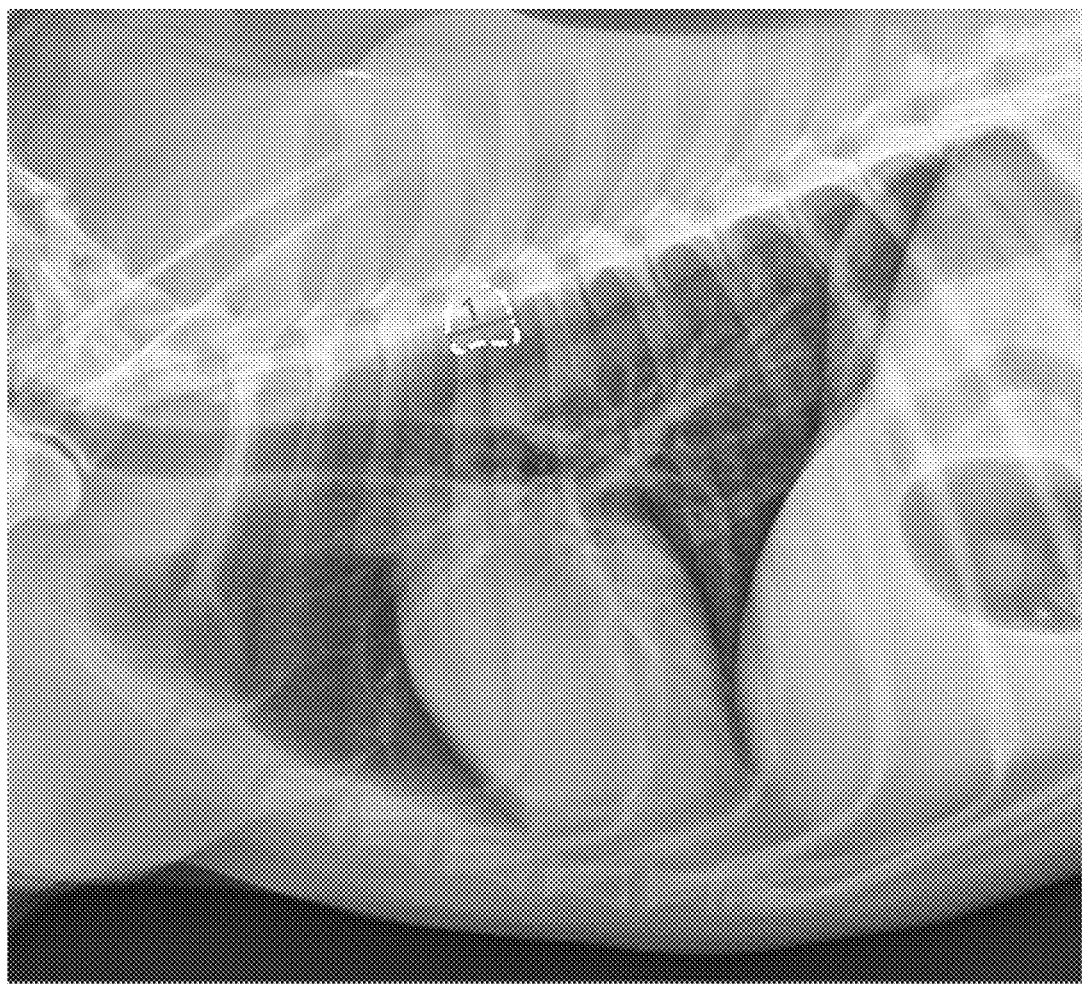
FIG. 5 is a view illustrating a value of a length of the region representing the specific thoracic vertebra of the animal at a position adjacent to the reference line.

In the present step, as shown in FIG. 3, a region representing the specific thoracic vertebra of the animal on the X-ray image of the animal may be automatically detected by using an image processing technique such as an edge detection algorithm and a value of the length of the region representing the specific thoracic vertebra of the animal may be automatically calculated. In the present step, the region representing the specific thoracic vertebra of the animal may be detected by using the image processing technique such as the edge detection algorithm, and the value of the length of the region representing the specific thoracic vertebra of the animal may be calculated in response to receiving a user input pointing to the specific thoracic vertebra of the animal on the X-ray image of the animal through an input interface 110. In the present step, the value of the length of the region representing the specific thoracic vertebra of the animal may be calculated in response to receiving, through the input interface 110, the user input specifying the length of the region representing the specific thoracic vertebra of the animal on the X-ray image of the animal, that is, in response to detecting, through the input interface 110, a user motion of drawing a reference line (See FIG. 4) corresponding to the length of the region representing the specific thoracic vertebra of the animal. A user may perform the motion of drawing a line as the reference line from a start point of the specific thoracic vertebra, which is a target for calculating the value of the length, to a disk between the corresponding thoracic vertebra and the next thoracic vertebra, that is, from the start point of the corresponding thoracic vertebra to a start point of the next thoracic vertebra. In this case, the value of the length of the region representing the specific thoracic vertebra of the animal is calculated as a value of a length of the reference line drawn by the user. In the present step, as shown in FIG. 5, the calculated value of the length of the region representing the specific thoracic vertebra of the animal may be displayed, on the X-ray image of the animal, in the region representing the specific thoracic vertebra of the animal or at a position adjacent to the reference line. In this case, when necessary, the user may also possibly adjust the reference line, or adjust the length of the reference line to appropriately correct the length of the reference line.

Figure 6:
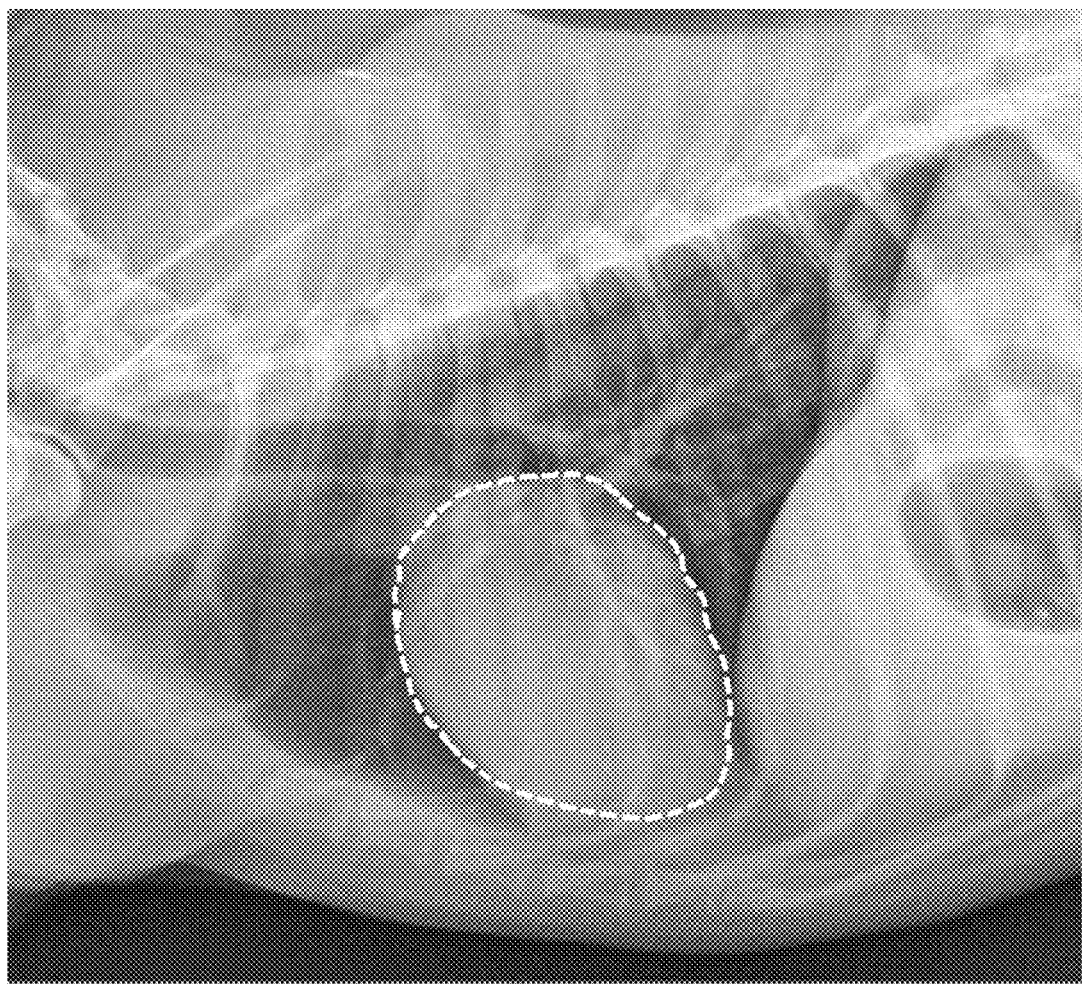
FIG. 6 is a view illustrating a region representing the heart of the animal automatically detected on the X-ray image of the animal.
Figure 7:
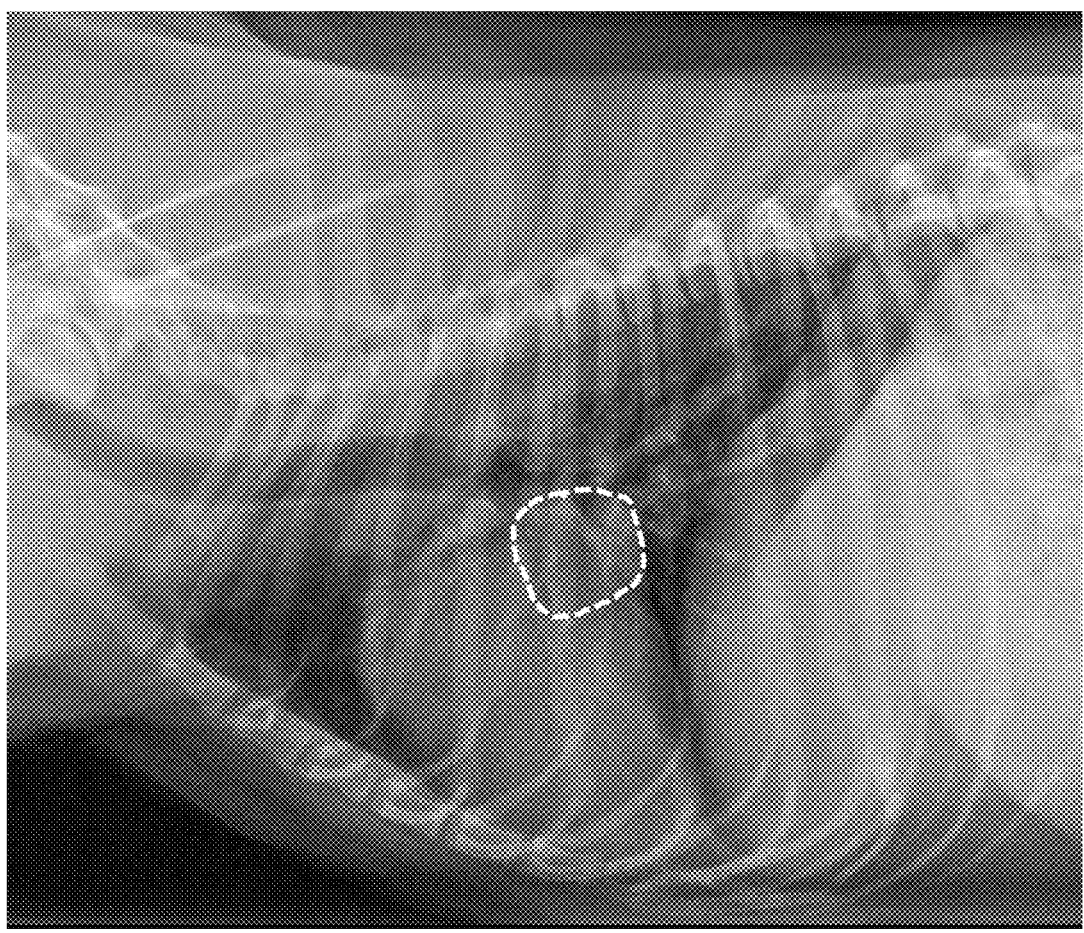
FIG. 7 is a view illustrating a region representing the left atrium of the heart of the animal automatically detected on the X-ray image of the animal.
Figure 8:
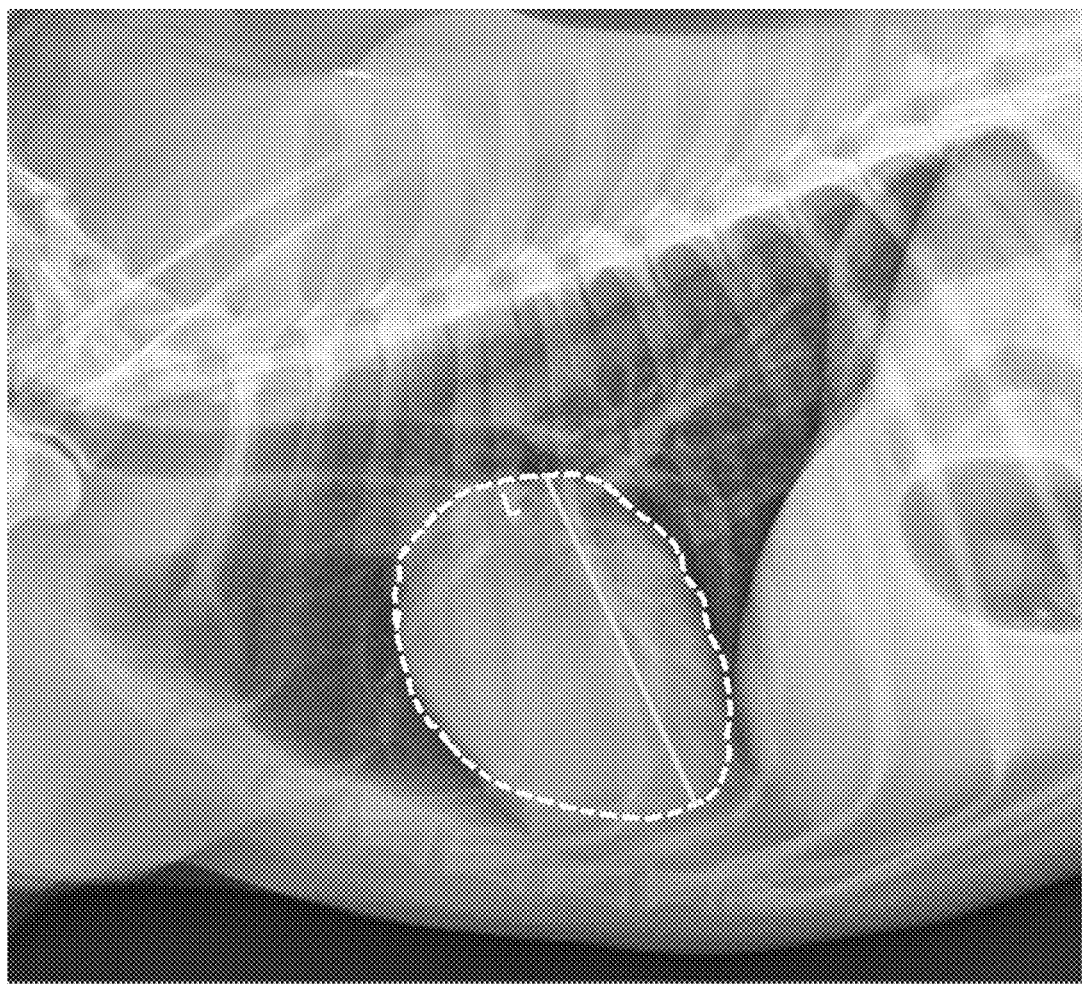
FIG. 8 is a view illustrating a reference line L in a long axis direction drawn by the user in the region representing the heart of the animal.

In step S220, a value of a length of the tissue of interest in the animal is calculated by using the X-ray image of the animal In the present step, as shown in FIG. 6, the region representing the heart of the animal may be automatically detected by using the image processing technique such as the edge detection algorithm on the X-ray image of the animal, a value of a length in a long axis direction of the region representing the heart of the animal may be automatically calculated, and a value of a length in a short axis direction perpendicular to the long axis direction of the region representing the heart of the animal may also be automatically calculated. In the present step, as shown in FIG. 7, a region representing the left atrium of the heart of the animal may be automatically detected by using the image processing technique such as the edge detection algorithm on the X-ray image of the animal, and a value of a length of the region representing the left atrium of the heart of the animal may be automatically calculated.

Figure 9:
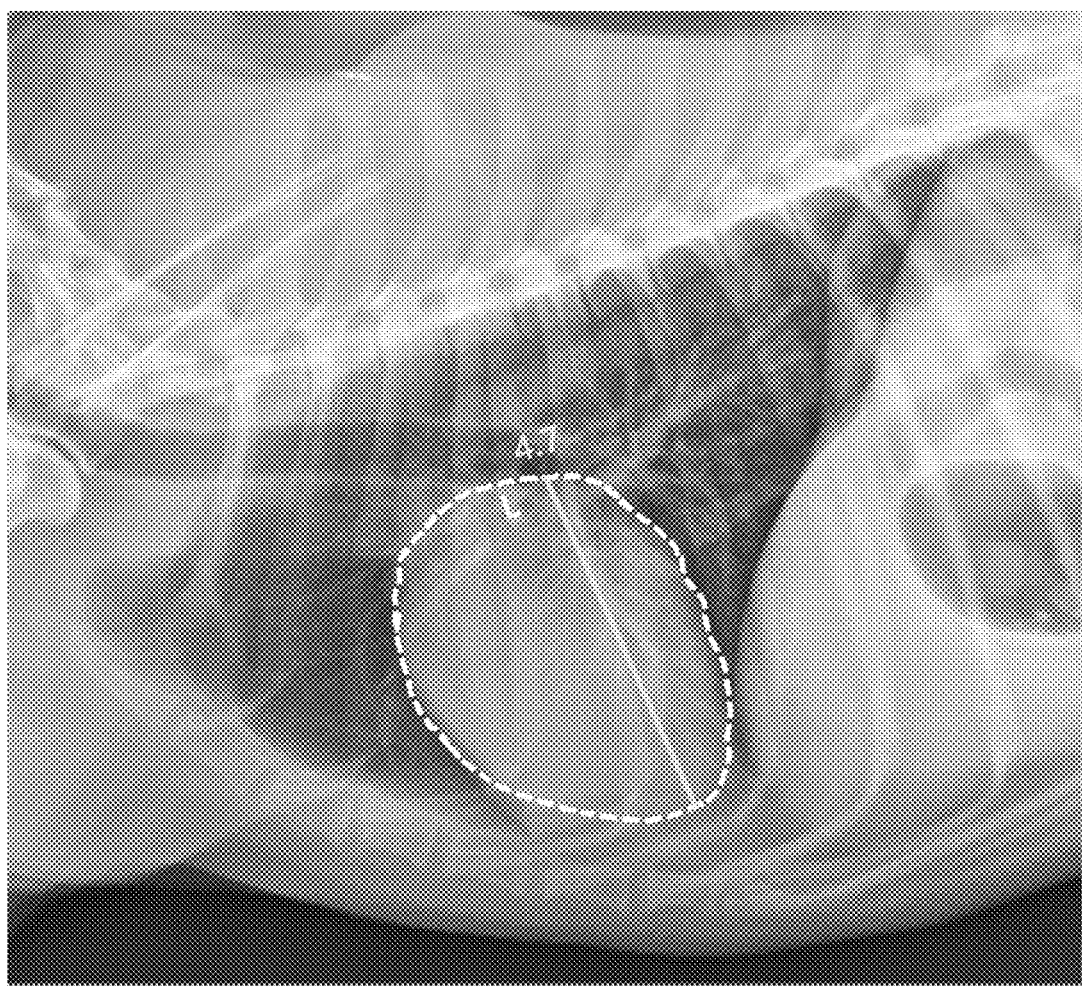
FIG. 9 is a view illustrating a value of a length in the long axis direction of the region representing the heart of the animal on the X-ray image of the animal at a position adjacent to the reference line L.

In the present step, a value of the length in the long axis direction of the region representing the heart of the animal may be calculated in response to receiving, through the input interface 110, a user input specifying the length in the long axis direction of the region representing the heart of the animal on the X-ray image of the animal, that is, in response to detecting, through the input interface 110, a user motion of drawing a reference line corresponding to the length in the long axis direction of the region representing the heart of the animal. The user may perform the motion of drawing a line as the reference line from a point (i.e., a reference point) of a ventral boundary of a carina to the apex of the heart (i.e., an end of the heart furthest from the reference point). In this case, the value of the length in the long axis direction of the region representing the heart of the animal is calculated as a value of a length of the reference line L drawn by the user. In the present step, as shown in FIG. 9, the calculated value of the length in the long axis direction of the region representing the heart of the animal may be displayed at a position adjacent to the reference line L on the X-ray image of the animal.

Figure 10:
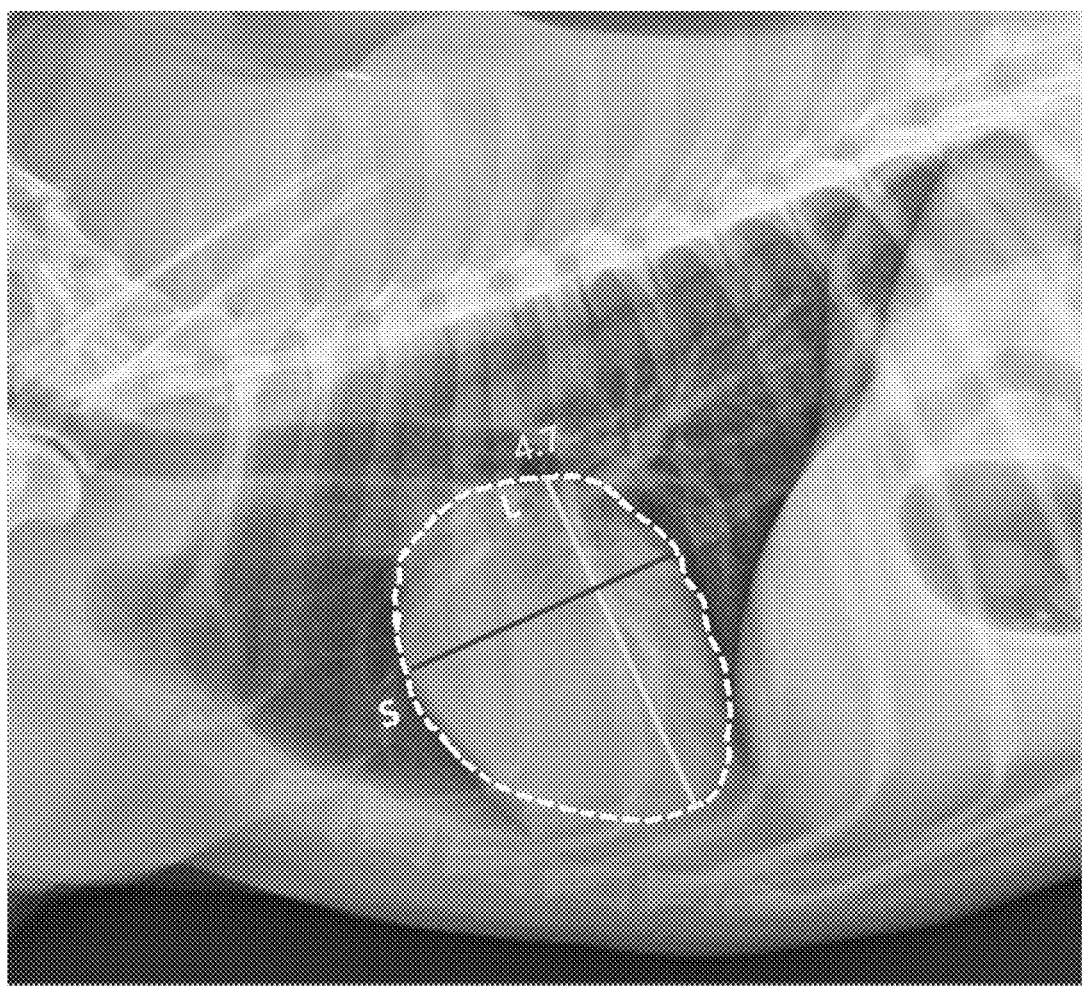
FIG. 10 is a view illustrating a reference line S in a short axis direction drawn by the user in the region representing the heart of the animal.
Figure 11:
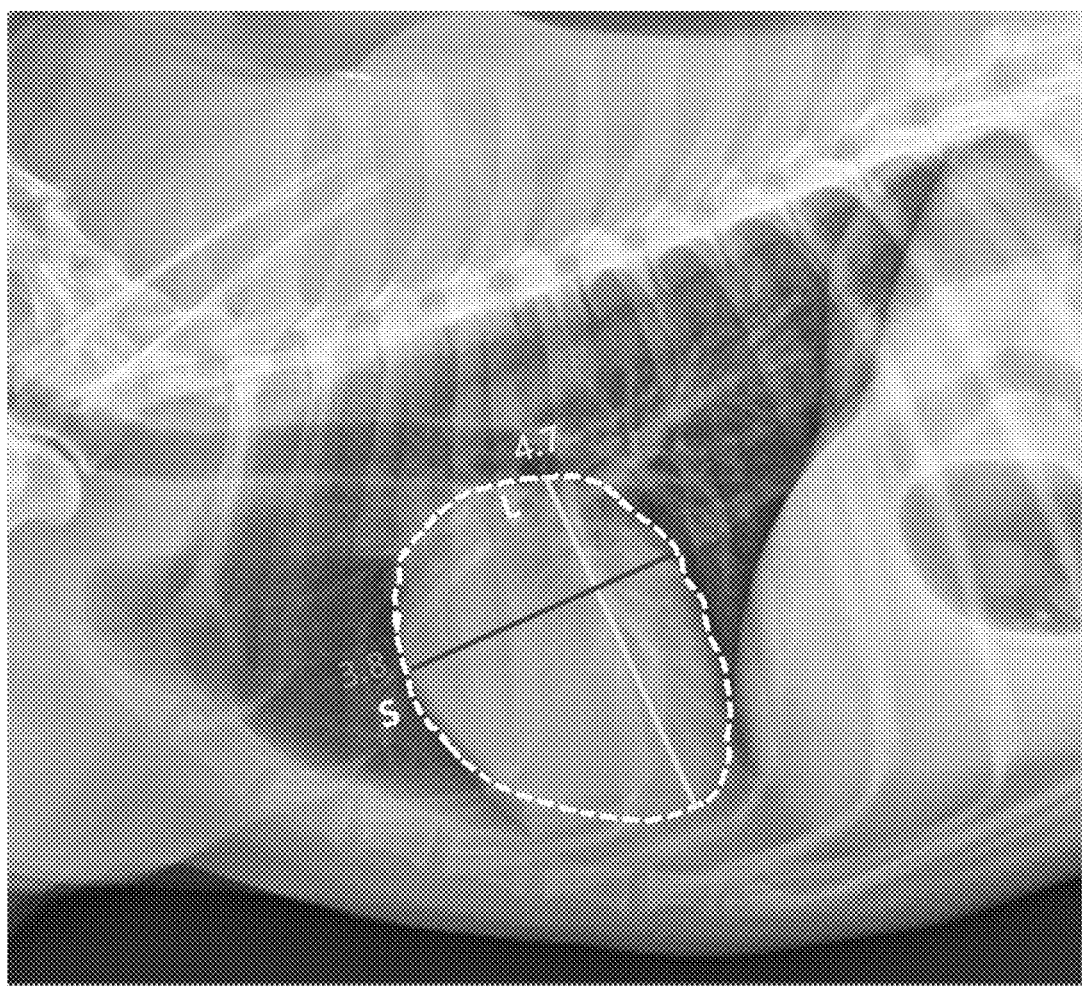
FIG. 11 is a view illustrating a value of a length in the short axis direction of the region representing the heart of the animal on the X-ray image of the animal at a position adjacent to the reference line S.

In the present step, a value of a length in a short axis direction of the region representing the heart of the animal may be calculated in response to receiving a user's input specifying the length in the short axis direction of the region representing the heart of the animal on the X-ray image of the animal, that is, in response to detecting the user's input of drawing a reference line corresponding to the length of the short axis direction in the region representing the heart of the animal. The user may perform a motion of drawing a reference line S (See FIG. 10) from a ventral contact point (i.e., a reference point) of the heart-aorta to a boundary point of the heart so as to be perpendicular to a predetermined length line in the long axis direction. In this case, the value of the length in the short axis direction of the region representing the heart of the animal is calculated as a value of a length of the reference line S drawn by the user. In the present step, as shown in FIG. 11, the calculated value of the length in the short axis direction of the region representing the heart of the animal may be displayed at a position adjacent to the reference line S on the X-ray image of the animal.

In the present step, the value of the length in the long axis direction of the region representing the heart of the animal may be automatically calculated by automatically detecting the apex of the heart in response to the user specifying the point on the ventral boundary of the carina of the animal as the reference point. In the present step, the value of the length in the short axis direction perpendicular to the long axis direction may be automatically calculated in response to the user specifying a ventral contact point of the heart-aorta of the animal as the reference point.

Figure 12:
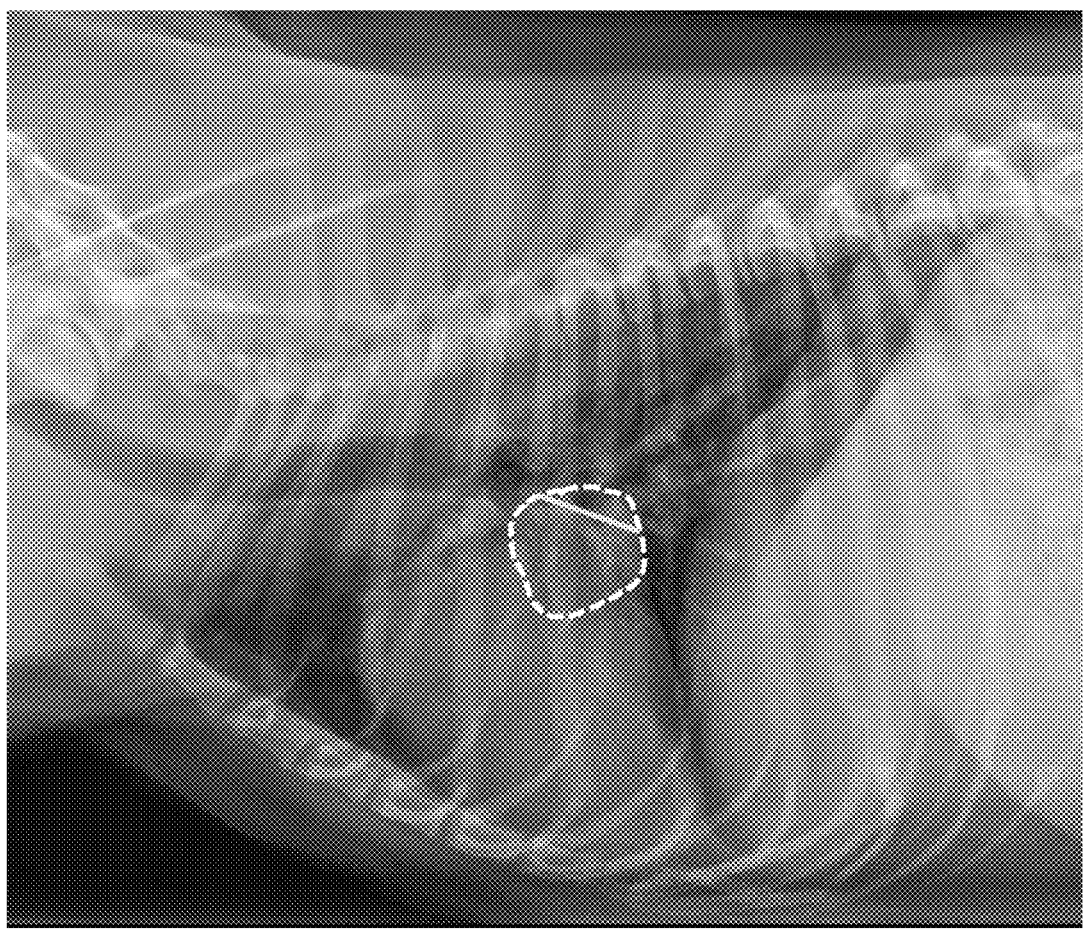
FIG. 12 is a view illustrating a reference line drawn by the user in the region representing the left atrium of the heart of the animal.
Figure 13:
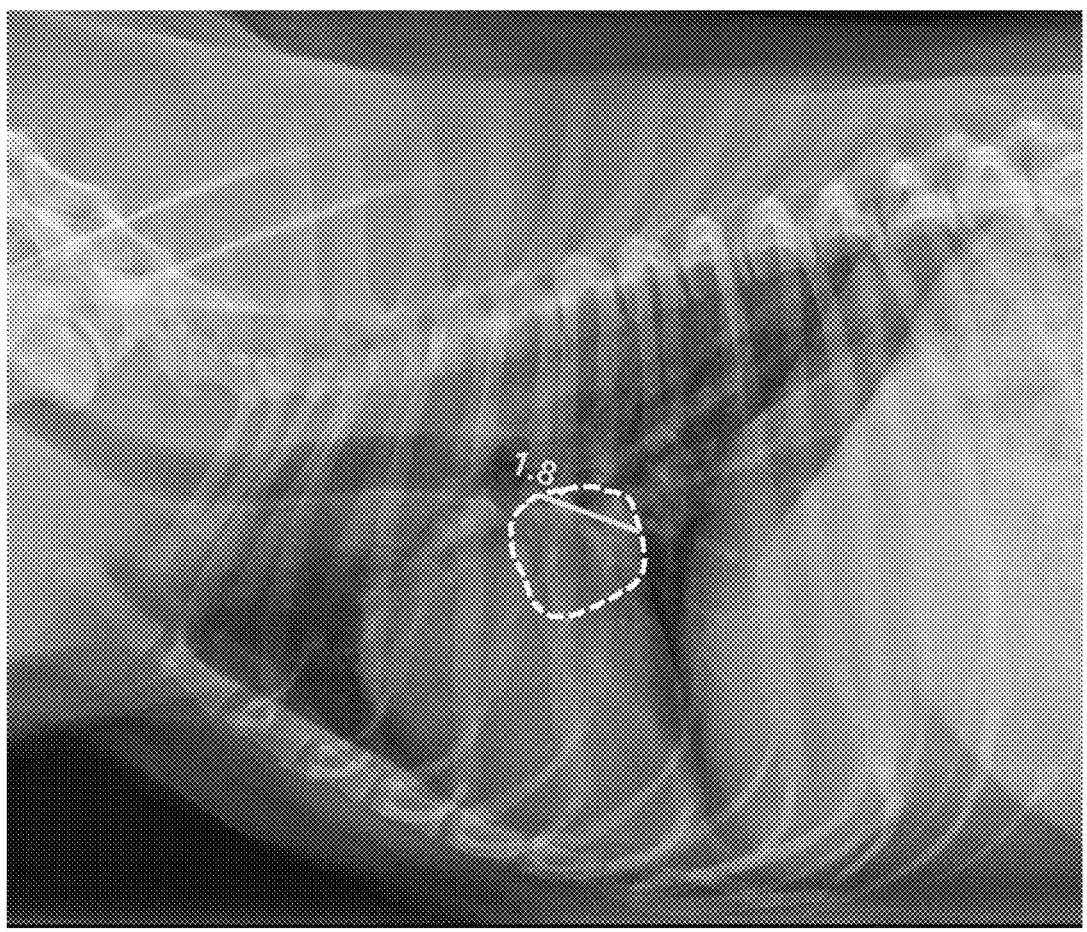
FIG. 13 is a view illustrating a value of a length of the region representing the left atrium of the heart of the animal on the X-ray image of the animal at a position adjacent to the reference line.

In the present step, a value of a length of a region representing the left atrium of the heart of the animal may be calculated in response to receiving, through the input interface 110, a user input specifying the length of the region representing the left atrium of the heart of the animal on the X-ray image of the animal, that is, in response to detecting, through the input interface 110, a user motion of drawing a reference line (See FIG. 12) corresponding to the length of the region representing the left atrium of the heart of the animal. Here, the value of the length of the region representing the left atrium of the heart of the animal is calculated as a value of a length of the reference line drawn by the user. In the present step, as shown in FIG. 13, the calculated value of the length of the region representing the left atrium of the heart of the animal may be displayed at a position adjacent to the reference line on the X-ray image of the animal.

In step S230, the size of the tissue of interest in the animal is quantified as a ratio of the value of the length of the tissue of interest in the animal to the reference value in the reference tissue in the animal. In the exemplary embodiment, a VHS index may be calculated by dividing a value obtained by adding the value of the length in the long axis direction of the region representing the heart of the animal to the value of the length in the short axis direction of the region representing the heart of the animal by the value of the length of the region representing the specific thoracic vertebra of the animal. Describing cases of the exemplary embodiment shown in FIGS. 5 and 11 as an example, the value of the length in the long axis direction of the region representing the heart of the animal is 4.7, the value of the length in the short axis direction of the region representing the heart of the ring axis is 3.8, and a value of a length of the region representing the fourth thoracic vertebra of the animal is 1, whereby the VHS index may be calculated as 8.5(=(4.7+3.8)/1). In the exemplary embodiment, a Vertebral Left Atrial Score (VLAS) index may be calculated by dividing the value of the length of the region representing the left atrium of the heart of the animal by the value of the length of the region representing the specific thoracic vertebra of the animal. Describing cases of the exemplary embodiment shown in FIGS. 5 and 13 as an example, the length of the region representing the left atrium of the heart of the animal is 1.8, and the value of the length of the region representing the fourth thoracic vertebra of the animal is 1, whereby the VLAS index may be calculated as 1.8(=(1.8)/1). In the present step, the calculated index values (i.e., the VHS and VLAS) may be respectively displayed, on the X-ray image of the animal, at the position adjacent to the region representing the heart of the animal and at the position adjacent to the region representing the left atrium of the heart of the animal.

In step S240, the quantified size of the tissue of interest, that is, the VHS index or the VLAS index is compared with a predetermined threshold, and a comparison result or a probability of cardiomegaly of the animal detected on the basis of the comparison result may be displayed to the user through a display 140. For example, when the VHS index is 8.7 to 10.7, this is meant to be within a normal range, so the corresponding result or the fact that the size of the heart of the animal is normal along with the corresponding result is displayed to the user through the display 140. In addition, when the VHS index exceeds 10.7, the corresponding result or the fact that the size of the heart of the animal has the probability of cardiomegaly is displayed to the user through the display 140. In addition, when the VLAS index is 2.3 to 2.5, this is meant to be within a normal range, so a corresponding result or the fact that the size of the heart of the animal is normal along with corresponding the result is displayed to the user through the display 140. When the VLAS index exceeds 2.5, a corresponding result or the fact that the size of the heart of the animal has the probability of cardiomegaly along with the corresponding result is displayed to the user through the display 140.

According to the exemplary embodiments disclosed herein, since the length of the specific thoracic vertebra of the animal shown on the X-ray image of the animal is used to quantify the size of the tissue of interest in the animal, the length of the specific thoracic vertebra of the animal on the X-ray image is not significantly different from an actual length thereof, even when an X-ray image of the animal is obtained on a state where the photographing postures of the animal are wrong. Therefore, even when the size of the tissue of interest in the animal is quantified on the basis of the X-ray image, the error in the quantified size of the tissue of interest is not large.

What is claimed is:

1. A method of quantifying a size of a tissue of interest of a animal, the method quantifying the size of the tissue of interest of the animal through a device configured to comprise a storage, an image processor, and a display by using an X-ray image of the animal and comprising:
   storing the X-ray image in the storage;
   displaying the X-ray image on the display;
   performing, by the image processor, processes of (i) calculating a reference value for a length of a reference tissue of the animal displayed on the X-ray image, (ii) calculating a value of a length in at least one specific direction of the tissue of interest of the animal displayed on the X-ray image, and (iii) quantifying the size of the tissue of interest as a ratio of the value of the length to the reference value; and
   displaying the quantified size of the tissue of interest on the display,
   wherein the reference tissue is a specific thoracic vertebra of the animal and the tissue of interest is the heart of the animal and,
   wherein the image processor performs processes of (i) identifying a first region representing the specific thoracic vertebra on the X-ray image, and calculating a value of a length of the first region as a reference value, (ii) identifying a second region representing the heart on the X-ray image, and calculating respective values of lengths in long axis and short axis directions of the second region as a value of a length of the heart, and (iii) quantifying the size of the tissue of interest by a value of dividing a value obtained by adding the respective values of the lengths in the long axis and short axis directions of the second region by the value of the length of the first region.

2. The method of claim 1, wherein the specific thoracic vertebra is any one of fourth to seventh thoracic vertebrae of the animal.

3. The method of claim 1, further comprising, after the quantifying the size of the tissue of interest:
   calculating, by the image processor, a comparison result by comparing the quantified size of the tissue of interest with a predetermined threshold; and
   displaying the comparison result on the display.

4. The method of claim 3, further comprising, after calculating the comparison result:
   calculating, by the image processor, whether an abnormality exists in the tissue of interest on the basis of the comparison result; and
   displaying, on the display, whether the abnormality exists.

5. A method of quantifying a size of a tissue of interest of a animal, the method quantifying the size of the tissue of interest of the animal through a device configured to comprise a storage, an image processor, and a display by using an X-ray image of the animal and comprising:

storing the X-ray image in the storage;

displaying the X-ray image on the display;

performing, by the image processor, processes of (i) calculating a reference value for a length of a reference tissue of the animal displayed on the X-ray image, (ii) calculating a value of a length in at least one specific direction of the tissue of interest of the animal displayed on the X-ray image, and (iii) quantifying the size of the tissue of interest as a ratio of the value of the length to the reference value; and displaying the quantified size of the tissue of interest on the display, wherein the reference tissue is a specific thoracic vertebra of the animal and the tissue of interest is the heart of the animal and, wherein the image processor performs processes of (i) identifying a first region representing the specific thoracic vertebra on the X-ray image, and calculating a value of a length of the first region as a reference value, (ii) identifying a second region representing the left atrium of the heart on the X-ray image, and calculating a value of a length of the second region as a value of a length of the left atrium of the heart, and (iii) quantifying the size of the tissue of interest by a value of dividing the value of the length of the second region by the value of the length of the first region.

6. A method of quantifying a size of a tissue of interest of a animal, the method quantifying the size of the tissue of interest of the animal through a device configured to comprise a storage, an image processor, and a display by using an X-ray image of the animal and comprising:

storing the X-ray image in the storage;

displaying the X-ray image on the display;

performing, by the image processor, processes of (i) calculating a reference value for a length of a reference tissue of the animal displayed on the X-ray image, (ii) calculating a value of a length in at least one specific direction of the tissue of interest of the animal displayed on the X-ray image, and (iii) quantifying the size of the tissue of interest as a ratio of the value of the length to the reference value; and displaying the quantified size of the tissue of interest on the display, wherein the reference tissue is a specific thoracic vertebra of the animal and the tissue of interest is the heart of the animal, wherein the device further comprises an input interface for receiving user inputs, wherein the method further comprises, after displaying the X-ray image on the display and before quantifying the size of the tissue of interest, inputting, through the input interface, each of a first user input configured to specify a length of a first region representing the specific thoracic vertebra on the X-ray image and a second user input configured to specify lengths in long axis and short axis directions of a second region representing the heart of the animal on the X-ray image, and wherein the image processor performs processes of (i) calculating a value of the length of the first region as a reference value in response to the first user input, (ii) calculating respective values of the lengths in the long axis and short axis directions of the second region as a value of a length of the heart in response to the second user input, and (iii) quantifying the size of the tissue of interest in the animal by a value of dividing a value obtained by adding the respective values of the lengths in the long axis and short axis directions of the second region by the value of the length of the first region.

7. A method of quantifying a size of a tissue of interest of a animal, the method quantifying the size of the tissue of interest of the animal through a device configured to comprise a storage, an image processor, and a display by using an X-ray image of the animal and comprising:

storing the X-ray image in the storage;

displaying the X-ray image on the display;

performing, by the image processor, processes of (i) calculating a reference value for a length of a reference tissue of the animal displayed on the X-ray image, (ii) calculating a value of a length in at least one specific direction of the tissue of interest of the animal displayed on the X-ray image, and (iii) quantifying the size of the tissue of interest as a ratio of the value of the length to the reference value; and displaying the quantified size of the tissue of interest on the display, wherein the reference tissue is a specific thoracic vertebra of the animal and the tissue of interest is the heart of the animal, wherein the device further comprises an input interface for receiving user inputs, wherein the method further comprises, after displaying the X-ray image on the display and before quantifying the size of the tissue of interest, inputting, through the input interface, each of a first user input configured to specify a length of a first region representing the specific thoracic vertebra on the X-ray image and a second user input configured to specify a length of a second region representing the left atrium of the heart on the X-ray image, and wherein the image processor performs processes of (i) calculating a value of the length of the first region as a reference value in response to the first user input, (ii) calculating a value of the length of the second region as a value of a length of the left atrium of the heart in response to the second user input, and (iii) quantifying the size of the tissue of interest in the animal by a value of dividing the value of the length of the second region by the value of the length of the first region.

8. A device for quantifying a size of a tissue of interest of a animal, the device quantifying the size of the tissue of interest in the animal by using an X-ray image of the animal and comprising:

a storage configured to store the X-ray image;

a display; and an image processor configured to calculate a reference value for a length of a reference tissue shown on the X-ray image, calculate a value of a length in at least one specific direction of the tissue of interest of the animal by using the X-ray image, and quantify the size of the tissue of interest by a ratio of a value of the length to the reference value, wherein the image processor is further configured to control the X-ray image and the quantified size of the tissue of interest to be displayed on the display, wherein the image processor is further configured to compare the quantified size of the tissue of interest with a predetermined threshold and calculate whether an abnormality of the tissue of interest exists on the basis of a comparison result, and the image processor is further configured to control at least one of the comparison result or whether the abnormality of the tissue of interest exists, which is calculated on the basis of the comparison result, to be displayed on the display.

* * * * *